(12) United States Patent
Yamada et al.

(10) Patent No.: US 8,708,556 B2
(45) Date of Patent: Apr. 29, 2014

(54) THERMAL ANALYZER

(75) Inventors: Kentaro Yamada, Chiba (JP); Shinya Nishimura, Chiba (JP); Hirohito Fujiwara, Chiba (JP)

(73) Assignee: SII NanoTechnology (JP)

( * ) Notice: Subject to any disclaimer, the term of this patent is extended or adjusted under 35 U.S.C. 154(b) by 127 days.

(21) Appl. No.: 13/065,687

(22) Filed: Mar. 28, 2011

(65) Prior Publication Data

US 2011/0235671 A1 Sep. 29, 2011

(30) Foreign Application Priority Data

Mar. 29, 2010 (JP) ................................. 2010-076380
Nov. 24, 2010 (JP) ................................. 2010-261720

(51) Int. Cl.
*G01N 25/00* (2006.01)

(52) U.S. Cl.
USPC ........................... 374/12; 374/10; 374/31

(58) Field of Classification Search
USPC .................................................. 374/10, 12, 31
See application file for complete search history.

(56) References Cited

U.S. PATENT DOCUMENTS

| | | | | | |
|---|---|---|---|---|---|
| 3,365,944 | A | * | 1/1968 | Hoagland et al. | 374/34 |
| 4,130,016 | A | * | 12/1978 | Walker | 374/34 |
| 5,509,733 | A | * | 4/1996 | Danley | 374/11 |
| 5,547,282 | A | * | 8/1996 | Pinhack et al. | 374/36 |
| 5,967,659 | A | * | 10/1999 | Plotnikov et al. | 374/11 |
| 6,742,926 | B1 | * | 6/2004 | Fesmire et al. | 374/45 |
| 8,066,429 | B2 | * | 11/2011 | Danley | 374/31 |
| 8,087,821 | B2 | * | 1/2012 | Danley | 374/12 |
| 2005/0053115 | A1 | * | 3/2005 | Nishimura | 374/12 |
| 2005/0190813 | A1 | * | 9/2005 | Schick | 374/10 |
| 2010/0322281 | A1 | * | 12/2010 | Lewis et al. | 374/34 |
| 2011/0054829 | A1 | | 3/2011 | Yamada | 702/136 |

FOREIGN PATENT DOCUMENTS

| | | |
|---|---|---|
| JP | 196311798 | 6/1963 |
| JP | 197133200 | 11/1971 |
| JP | 19734072 | 2/1973 |
| JP | 19734073 | 2/1973 |
| JP | 197928679 | 3/1979 |
| JP | 10246713 | 9/1998 |
| JP | 2001183319 | 7/2001 |
| JP | 2005227188 | 8/2005 |
| JP | 2005345333 | 12/2005 |
| JP | 2008530560 | 8/2008 |
| JP | 2011053077 | 3/2011 |

OTHER PUBLICATIONS

Patent Abstracts of Japan, publication No. 2005-345333, publication date Dec. 15, 2005.
Abstract, publication No. WO/2006-086708, publication date Aug. 17, 2006.

* cited by examiner

*Primary Examiner* — Mirellys Jagan
(74) *Attorney, Agent, or Firm* — Adams & Wilks

(57) ABSTRACT

A thermal analyzer heats and cools a sample placed inside a furnace for measuring a thermal characteristic of the sample during heating and cooling. The thermal analyzer has a multilayer structure for covering the furnace and its surroundings so as to isolate the furnace and its surroundings from an external environment. The multilayer structure includes a multilayer wall with two layers formed of a material having high thermal conductivity and heat dissipation property. The two layers are spaced apart from one another to provide therebetween an interlayer that contains a substance having a heat capacity substantially equal to a gas contained in the furnace so that heat transfer between the two layers is minimized.

20 Claims, 3 Drawing Sheets

F I G . 1
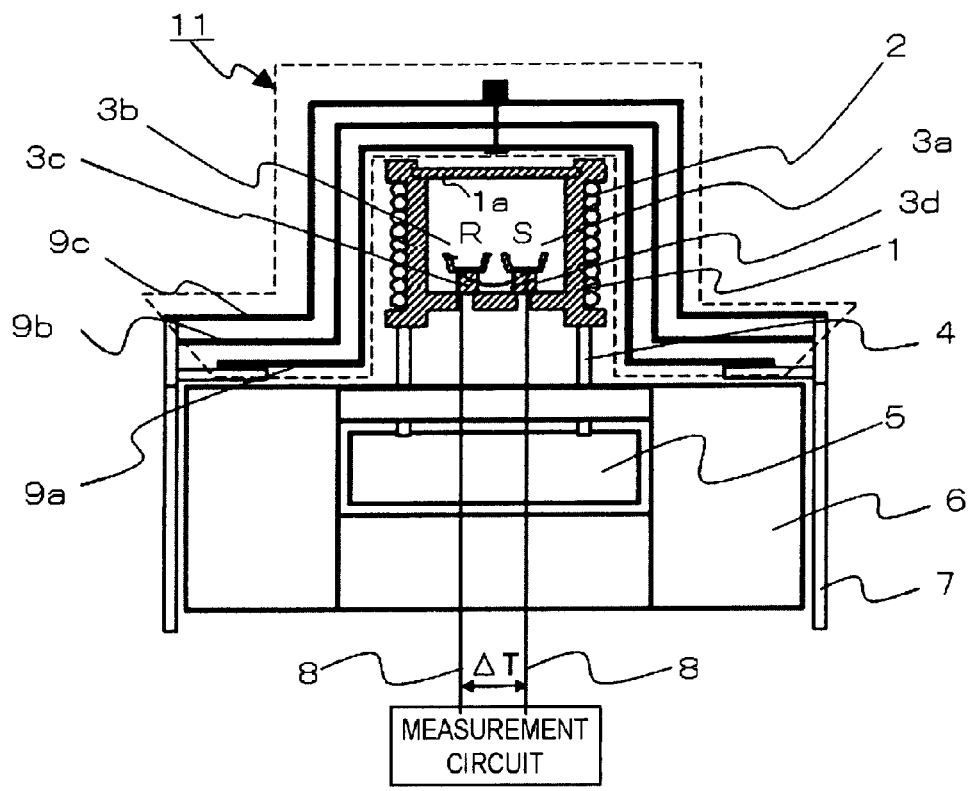

THERMAL ANALYZER

BACKGROUND OF THE INVENTION

1. Field of the Invention

The present invention relates to a thermal analyzer, and more particularly, to heat insulation structure inside a furnace of a thermal analyzer.

2. Description of the Related Art

As an example of the thermal analyzer, a differential scanning calorimeter (hereinafter, referred to as DSC) is a thermal analyzer that changes temperature of a furnace provided inside the apparatus according to a constant temperature rate program, to thereby measure a difference in temperature between a sample and a reference substance placed inside the furnace (heat flux type, which is one type of DSCs), or a difference in thermal energy, which is applied so as to eliminate the difference in temperature between the sample and the reference substance (power compensation type, which is another type of DSCs).

In order that the DSC stably detect the difference in temperature between the sample and the reference substance or the difference in thermal energy necessary to maintain the difference in temperature therebetween to zero, it is important that a detector and a furnace portion having the detector mounted thereon are provided in a stable environment in which no direct influence of temperature disturbance is imposed. Further, from a viewpoint of providing a measurer with the convenience of being able to conduct a measurement in a wide temperature range, in order to realize a wide measurement temperature range from a desired high temperature to a temperature lower than room temperature (for example, −150° C. to 750° C.), it is also important that heat exchange between the furnace portion and the outside is suppressed to perform heating and cooling efficiently.

For the reasons described above, general DSCs are designed so that the detector and the furnace portion having the detector mounted thereon are isolated from the external environment and insulated from heat.

For example, there is proposed a heat flux DSC structured so that the entire furnace is covered with a partition wall and is further covered with a heat insulation case in which a heat insulation material is loaded into a space between an outer frame and an inner frame. The heat insulation case has an effect of suppressing influence of external temperature disturbance to provide a stable baseline, resulting in a high-sensitivity DSC measurement (see Japanese Patent Application Laid-open No. 2005-345333).

Further, for example, the power compensation DSC is structured so that temperature control can be performed both on a furnace provided with a heater for applying thermal energy to a sample and a reference substance and on a thermal shield arranged outside the furnace. By controlling temperature of the thermal shield, that is, by controlling the surrounding environment of the furnace, a stable baseline can be obtained (see Japanese Patent Translation Publication No. 2008-530560).

In the DSC measurement, sensitivity, resolution, and a noise level serve as performance indicators. In addition, baseline reproducibility is an important indicator. The "reproducibility" herein refers to "consistency of measurement baselines in repetition, which are obtained through repetitive measurements using the same temperature program".

In a case of low (poor) baseline reproducibility, even through the repetitive measurements using the same temperature program, the baseline changes from measurement to measurement, which raises difficulty in comparing measurement results. In a case of high (good) baseline reproducibility, on the other hand, results are easy to compare between measurements, with the result that more detailed thermal changes of the sample can be captured and reliability of measurement results themselves is increased.

One of important factors of influence on the baseline reproducibility is a temperature environment given around the furnace, as well as accuracy of temperature control for the furnace that houses a detection portion. Even in a case where accurate temperature control is performed on the furnace, if the temperature environment given around the furnace fluctuates from measurement to measurement, the fluctuation of the temperature environment inevitably influences the baseline reproducibility as a measurement-based fluctuation in baseline, particularly for the high-sensitivity DSC that measures temperature or thermal energy.

However, in a thermal analyzer described in the embodiment of Japanese Patent Application Laid-open No. 2005-345333, a metal heat insulation shield and a heat insulation cover in which a heat insulation material is loaded are provided for the purpose of isolation and heat insulation of the furnace and its surroundings. In this embodiment, when repetitive measurements involving heating and cooling of the furnace are performed according to a constant temperature program, the heat insulation shield and the heat insulation cover, which are arranged around the furnace, are also heated and cooled due to the influence thereof, and temperature changes thereof occur with a delay having a fixed time constant. This is because the overall heat insulation structure around the furnace, including the heat insulation shield and the heat insulation cover, has low thermal conductivity for suppressing disturbance and a predetermined heat capacity due to the structure itself. For example, when the furnace control is switched from heating to cooling, the heat insulation material around the furnace is not so cooled as compared to the furnace itself, resulting in a delay in temperature drop. Therefore, actual temperature inside the furnace exhibits thermal hysteresis due to repetitive heating and cooling.

Due to the thermal hysteresis of the heat insulation structure, the temperature environment around the furnace is changed in the repetitive measurements, and as a result, there arises a problem of fluctuation in baseline.

In the case of the technology described in Japanese Patent Translation Publication No. 2008-530560, a thermal shield whose temperature can be controlled is provided around the furnace. It is considered that by controlling temperature of the thermal shield as appropriate, the measurement-based change of the temperature environment around the furnace does not become larger. In this case, however, it is necessary to control temperature of the thermal shield according to the state of the furnace, and hence there arises a problem of more complicated apparatus structure and control system as compared to the general case. Further, it is necessary to allocate cooling performance of a cooling device also to the thermal shield in addition to the furnace whose temperature is originally desired to be controlled, and hence the cooling rate, the lowest reachable temperature, and the like are limited as compared to the case where only the furnace is simply cooled.

SUMMARY OF THE INVENTION

The present invention has been made in order to solve the above-mentioned problems, and it is therefore an object of the present invention to provide a thermal analyzer which does not need any complicated control and structure, and is capable of a measurement with high baseline reproducibility.

In order to achieve the above-mentioned object, in a thermal analyzer according to the present invention, the furnace in which a sample is received and its surroundings are covered with a wall member, and accordingly the furnace is isolated from the outside. The wall member has a multilayer structure of at least two layers, and a layer having a heat insulation effect is provided between the layers constituting the wall member. Further, the heat insulation layer is set as a gas layer, and there is used an interlayer material which does not have an excessively high heat capacity as compared to a gas.

In the multilayer wall member around the furnace, a metal may be used, such as stainless steel, for the first layer as a material having heat resistance and corrosion resistance, and for the second and subsequent layers, a metal material having relatively high thermal conductivity and heat dissipation property may be used, such as aluminum or copper. Further, a gas such as air or nitrogen may be used for the interlayer of the wall member. This structure avoids using, around the furnace, a solid heat insulation material having a relatively high heat capacity as compared to a gas, and hence the heat capacity of the heat insulation structure around the furnace becomes relatively lower. Accordingly, when the measurement is repeated, the heat insulation structure around the furnace allows a relatively quick temperature change as compared to the structure using the solid heat insulation material, and hence the thermal hysteresis due to a delay in response tends to be reduced. Thus, the change of the temperature environment around the furnace is suppressed to a small value. Further, a gas which is not high in thermal conductivity is used for the interlayer of the multilayer wall member, which realizes sufficient heat insulation property and small influence of disturbance, resulting in a measurement with a wide temperature range. As a result, the thermal analyzer capable of obtaining a baseline exhibiting high reproducibility in the wide temperature range is realized.

As described above, according to the present invention, the heat insulation structure around the furnace is not excessively high in heat capacity as compared to a gas, and hence there is produced an effect of reducing the thermal hysteresis of the heat insulation structure around the furnace, which occurs at the time of repetitive measurements. As a result, the change of the temperature environment around the furnace in the repetitive measurements is suppressed, with the result that data exhibiting stable and high baseline reproducibility can be obtained.

BRIEF DESCRIPTION OF THE DRAWINGS

In the accompanying drawings:

FIG. 1 is a structural diagram according to an embodiment of the present invention;

DETAILED DESCRIPTION OF THE PREFERRED EMBODIMENT

Figure 2:
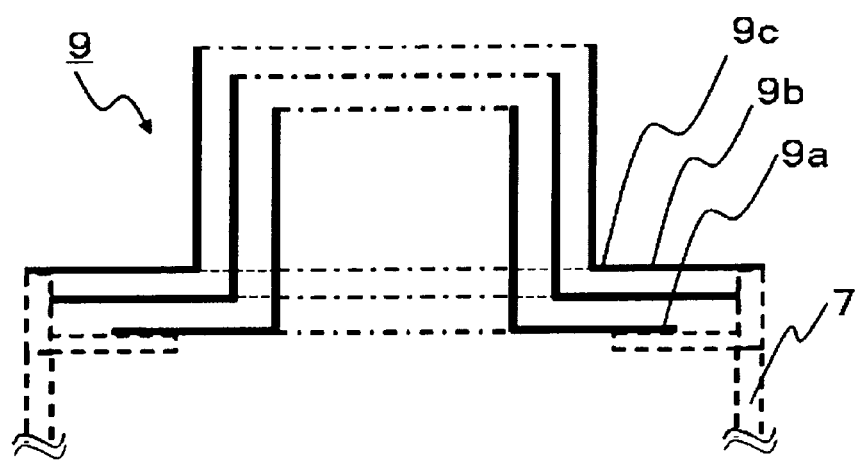
FIG. 2 is a schematic diagram of structure of a multilayer wall according to the embodiment of the present invention.

Hereinbelow, referring to the drawings, a thermal analyzer according to the present invention is described by taking a DSC as an example. Note that, dimensions of components or the like are changed as appropriate as long as the ratio thereamong does not lead to any problem, in particular.

FIG. 1 illustrates the apparatus structure of the DSC according to an embodiment of the present invention.

The DSC includes a furnace 1, and the furnace 1 has a furnace lid 1a removably arranged in its upper portion. Further, a heater coil 2 is wound around the furnace 1 so as to heat the furnace 1. Although not illustrated, the furnace 1 has a cover attached therearound so that the heater coil 2 is not exposed. There are arranged, inside the furnace 1, a sample holder 3a for receiving a sample substance, a reference substance holder 3b for receiving a reference substance and thermal resistance 3C for becoming a heat flow path of those each holders and the furnace. Both holders 3a, 3b have thermocouples connected thereto, which constitute a differential heat flow detection portion 3d for detecting a temperature difference between the holders. Thermocouple wires 8 extending from the heat flow detection portion 3d are connected to a measurement circuit, and detected signals are recorded in the form of a DSC curve after being amplified.

A cooling block 5 arranged below the furnace 1 is structured so that a cooling device can be connected thereto as necessary, and is connected to the furnace 1 through an intermediation of a heat resistant material 4. When cooling the furnace 1, the cooling block 5 is cooled to function as a heat sink. The cooling block 5 and its surroundings are sufficiently insulated from heat of an external environment by a heat insulation material, and the cooling block 5 is housed in a jacket case 7, which prevents dewing or the like caused at the time of cooling.

Embodiment

Next, referring to the drawings, the heat insulation structure around the furnace of the present invention is described.

In FIG. 1, the furnace 1 has a multilayer wall 9 arranged therearound. The multilayer wall 9 is formed of a plurality of layers (in this case, three layers) so as to cover the entire furnace 1. In this case, the multilayer wall 9 has a cylindrical shape in which the cross section thereof has a round shape.

FIG. 2 is a schematic diagram of the multilayer wall 9 alone.

A first layer wall 9a is formed of stainless steel as a material having heat resistance and corrosion resistance. The first layer wall 9a has a thickness of 0.5 mm, and has a cylindrical shape in which the diameter thereof is set so that a gap between the first layer wall 9a and the furnace 1 is 1 mm. The upper and lower portions of the cylinder each have an opening.

A second layer wall 9b and a third layer wall 9c are each formed of aluminum as a material having relatively high thermal conductivity and heat dissipation property. The second layer wall 9b and the third layer wall 9c each have a thickness of 1 mm, and their diameters are each set so as to be 20 mm larger than the inner layer diameter. The second layer wall 9b and the third layer wall 9c are each fixed to the jacket case 7 of the apparatus body so that a distance of the interlayer becomes 10 mm. The layers are heat-separated so that heat transfer due to solid conduction between the layers becomes as small as possible. In order to increase the heat separation property, there is employed, for the interlayer, a gas having relatively lower thermal conductivity as compared to the solid thermal conduction (in this case, air having atmospheric pressure). The multilayer wall 9 described above is combined with a multilayer lid 10 described later to provide a multilayer structure 11, with the result that the flow of the air within the space is restricted between the layers and the air functions as a heat insulation layer. As described above, the multilayer structure 11 including the gas layer has heat insulation property against the external environment, with the result that the furnace can be isolated from the external environment and therefore insulated from heat.

In fixing the layer walls to the jacket case 7, the layer walls are bonded to the jacket case 7 so that the space between the layers is sealed with high reliability.

In this embodiment, the thickness of the wall member is set to 1 mm, but the optimal thickness varies depending on the thermal conductivity of the material. In a case of a metal wall member, the thickness preferably ranges from 0.1 mm to 3 mm, and more preferably, from 0.3 mm to 2 mm, approximately.

In this embodiment, the thickness (distance between the second and third layer walls $9b$, $9c$) of the interlayer is set to 10 mm, but from the above-mentioned viewpoint of solid thermal conduction and heat insulation, the range of the distance of the interlayer preferably ranges from 0.5 mm to 50 mm, and more preferably, from 1.0 mm to 30 mm. When the distance of the interlayer is 0.5 mm or less, the thermal conduction becomes highly effective. When the distance of the interlayer is 50 mm or more, the layer walls contribute less to the heat insulation property and in the case where a gas is loaded into the interlayer, influence of convection thereof becomes larger, with the result that the stability of the baseline is likely to be lost. When the number of layers or the distance of the interlayer is decreased, the heat insulation property tends to be decreased, whereas when the number of layers or the distance of the interlayer is increased, the heat insulation property tends to be increased. The number of layers is not limited to three as long as the layers have heat insulation property necessary for the apparatus. For example, a multilayer formed of two, four, or more layers may be employed, and two to five layers are preferred. This is because a single layer cannot form the above-mentioned heat insulation layer and hence is hard to obtain the heat insulation property necessary for the apparatus, whereas too many layers contribute less to improvement in heat insulation effect necessary for the apparatus and result in larger outline dimensions of the apparatus and lower cost effectiveness.

The material used for the interlayer only needs to be a substance which does not have an excessively high heat capacity as compared to the gas but has a heat capacity substantially equal to that of the gas. Thus, the material is not limited to the air as in the above description using the gas, and may be a material formed of an interlayer substance that produces the effect of the present invention.

It is noted that this embodiment has described that the multilayer wall 9 has its cross section in a round shape, but the present invention is not limited thereto and the cross section may have a polygonal shape.

Figure 3:
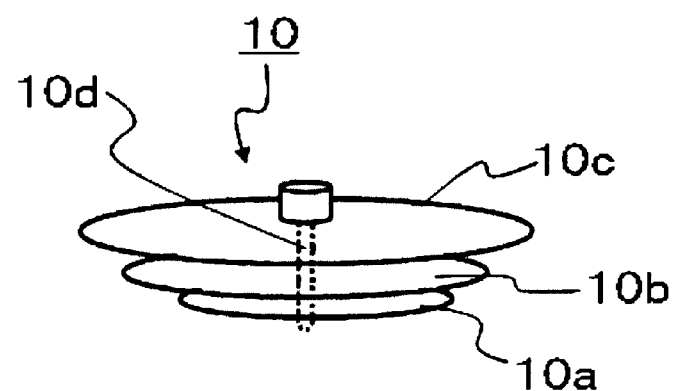
FIG. 3 is a schematic diagram of structure of a multilayer lid according to the embodiment of the present invention.

FIG. 3 is a structural diagram of the multilayer lid 10. The multilayer lid 10 is formed of the same number of layers (in this case, three) as the cylindrical wall member. In order that the layers of the multilayer lid 10 have the same structure as the cylindrical metal wall member 9, a first layer lid $10a$ is formed of stainless steel as a material having heat resistance and corrosion resistance, and is a disk having a thickness of 0.5 mm, while a second layer lid $10b$ and a third layer lid $10c$ are each formed of aluminum as a material having relatively high thermal conductivity and heat dissipation property, and are each a disk having a thickness of 1 mm. The layer lids $10a$, $10b$, and $10c$ constituting the multilayer lid 10 are integrated by a shaft $10d$, which is inserted into a through-hole provided at the center. With the shaft $10d$, the lids may be removed through a single removal operation, which saves labor and time for sample replacement and the like as compared to a case of separate lids of layers. It is noted that in order to suppress the thermal conduction, a stainless steel material having relatively low thermal conductivity is used for the shaft $10d$, and the diameter thereof is as small as 1 mm.

Figure 4:
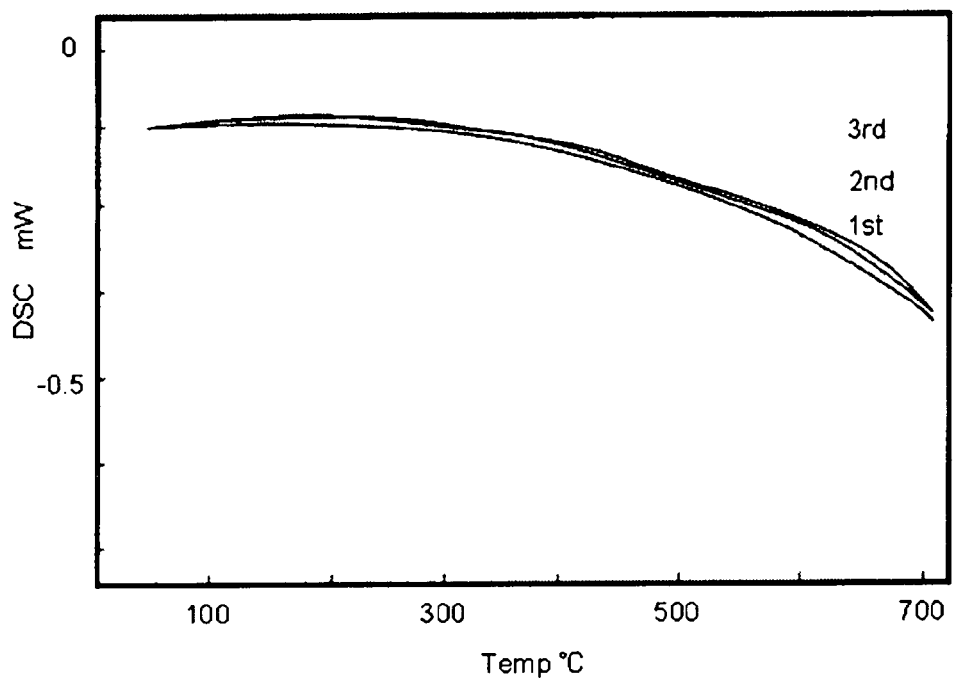
FIG. 4 is a graph showing an example of DSC baseline reproducibility of an apparatus according to the embodiment of the present invention.
Figure 5:
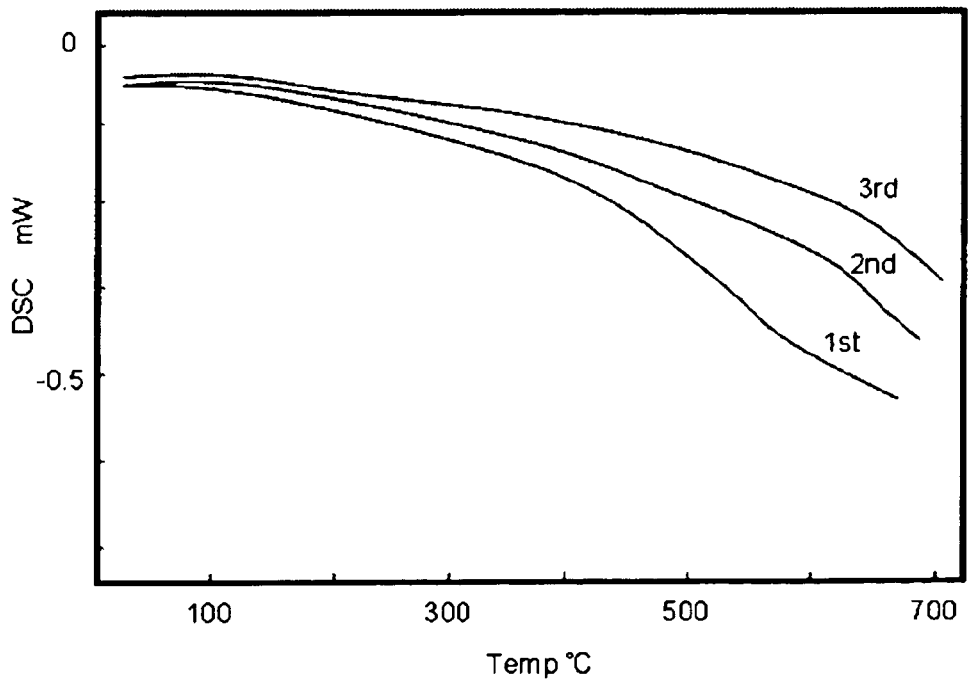
FIG. 5 is a graph showing an example of DSC baseline reproducibility in a conventional technology.

FIG. 4 is a graph showing an example of DSC baseline reproducibility obtained in a case where the multilayer structure 11 according to the present invention is arranged around the furnace and is used for heat insulation. FIG. 5 is a graph showing an example of DSC baseline reproducibility obtained in a conventional case where the heat insulation material is used around the furnace.

FIGS. 4 and 5 each show an example of a case where temperature is raised at a constant rate, with the axis of ordinate representing a heat flow difference and the axis of abscissa representing temperature. In the case of the structure in which the heat insulation material is used around the furnace as in the conventional technology, as illustrated in FIG. 5, DSC baselines obtained through repetitive measurements (first to third temperature rise baselines in the repetitive measurements) exhibit a large divergence and hence the reproducibility is low.

In the case where the multilayer structure 11 according to the present invention is arranged around the furnace and is used for heat insulation, on the other hand, as illustrated in FIG. 4, DSC baselines obtained through repetitive measurements (first to third temperature rise baselines in the repetitive measurements) exhibit quite a smaller divergence and hence the reproducibility is high.

As described above, this embodiment has described the case where the present invention is applied to the DSC, but the applicable range of the present invention is not limited thereto. For example, the present invention is also applicable to a thermogravimetry (TG) or a differential thermal analysis (DTA).

What is claimed is:

1. A thermal analyzer that heats and cools a sample placed inside a furnace for measuring a thermal characteristic of the sample during heating and cooling, the thermal analyzer comprising: a multilayer structure for covering the furnace and its surroundings so as to isolate the furnace and its surroundings from an external environment, the multilayer structure including a multilayer wall comprised of two layers formed of a material having high thermal conductivity and heat dissipation property, the two layers being spaced apart from, and not in direct contact with, one another to provide therebetween an interlayer space that contains a substance having a heat capacity substantially equal to a gas contained in the furnace so that heat transfer between the two layers is minimized; and a cooling block configured to be connected to a cooling device for cooling the furnace, the cooling block being arranged below the furnace through intermediation of a heat resistant material and having a heat insulation material covering the cooling block and its surrounding so as to insulate the cooling block from heat of the external environment.

2. A thermal analyzer according to claim 1, wherein the two layers are spaced-apart from one another at a distance ranging from 0.5 mm to 50 mm.

3. A thermal analyzer according to claim 1, wherein the thermal analyzer comprises a differential scanning calorimeter.

4. A thermal analyzer according to claim 1, wherein the substance that is contained in the interlayer comprises a gas.

5. A thermal analyzer according to claim 4, wherein the two layers are spaced-apart from one another at a distance ranging from 0.5 mm to 50 mm.

6. A thermal analyzer according to claim 1, wherein each of the two layers of the multilayer wall comprises a metal wall member.

7. A thermal analyzer according to claim 6, wherein a thickness of each of the metal wall members ranges from 0.1 mm to 3 mm.

8. A thermal analyzer according to claim 1, wherein the multilayer structure further includes a multilayer lid including two layer lids mounted to respective ones of the two layers of the multilayer wall.

9. A thermal analyzer according to claim 8, wherein the multilayer wall further comprises another layer formed of a material having heat and corrosion resistance; and wherein the multilayer lid further includes another layer lid mounted on the another layer.

10. A thermal analyzer according to claim 1, wherein the multilayer wall further comprises another layer formed of a material having heat and corrosion resistance.

11. A thermal analyzer according to claim 10, wherein the another layer is spaced apart from the furnace at a distance of 1 mm.

12. A thermal analyzer according to claim 10, wherein each of the two layers is formed of aluminum and the another layer is formed of stainless steel.

13. A thermal analyzer according to claim 10, wherein each of the two layers and the another layer has a thickness in the range of from 0.1 mm to 3 mm.

14. A thermal analyzer according to claim 10, wherein each of the two layers and the another layer has a thickness in the range of from 0.3 mm to 2 mm.

15. A thermal analyzer comprising:
  a furnace configured to receive therein a sample that is to be heated and cooled for measuring a thermal characteristic of the sample;
  a heat insulation structure covering the furnace so as to isolate the furnace from variations in temperature external to the thermal analyzer, the heat insulation structure having a multilayer wall formed of a plurality of wall layers including two wall layers spaced apart from, and not in direct contact with, one another to form a space between the two wall layers, and a gas layer formed in the space between the two wall layers and having a heat capacity substantially equal to a gas contained in the furnace so that heat transfer between the two wall layers is minimized;
  a cooling block configured to be connected to a cooling device for cooling the furnace, the cooling block being arranged below the furnace through intermediation of a heat resistant material; and
  a heat insulation material covering the cooling block and its surrounding so as to insulate the cooling block from heat of the external environment.

16. A thermal analyzer according to claim 15, wherein the two wall layers are spaced-apart from one another at a distance ranging from 0.5 mm to 50 mm.

17. A thermal analyzer according to claim 15, wherein the gas layer is formed of air.

18. A thermal analyzer according to claim 15, wherein each of the two wall layers and the another wall layer has a thickness in the range of from 0.1 mm to 3 mm.

19. A thermal analyzer according to claim 15, wherein the plurality of wall layers further includes another wall layer spaced apart from the furnace at a distance closer than that of the two wall layers.

20. A thermal analyzer according to claim 19, wherein each of the two wall layers is formed of aluminum and the another wall layer is formed of stainless steel.

* * * * *